(12) United States Patent
Malmqvist

(10) Patent No.: US 6,432,694 B1
(45) Date of Patent: Aug. 13, 2002

(54) CARTRIDGE AND SYSTEM FOR STORING AND DISPENSING OF REAGENTS

(75) Inventor: Mats Malmqvist, Uppsala (SE)

(73) Assignee: Alphahelix AB, Uppsala (SE)

( * ) Notice: Subject to any disclaimer, the term of this patent is extended or adjusted under 35 U.S.C. 154(b) by 0 days.

(21) Appl. No.: 09/254,681

(22) PCT Filed: Sep. 16, 1997

(86) PCT No.: PCT/SE97/01562

§ 371 (c)(1),
(2), (4) Date: Jun. 10, 1999

(87) PCT Pub. No.: WO98/10866

PCT Pub. Date: Mar. 19, 1998

(30) Foreign Application Priority Data

Sep. 16, 1996 (SE) ................................. 9603400
May 16, 1997 (SE) ................................. 9701861

(51) Int. Cl.⁷ .......................... C12M 1/00; B01L 3/00
(52) U.S. Cl. .................. 435/286.5; 435/288.4; 436/177; 436/180; 422/72; 422/100
(58) Field of Search .............. 435/6, 287.2, 286.5, 435/287.3, 287.6, 288.1, 288.3, 288.4; 422/72, 100, 101, 102; 494/17; 141/34, 237, 238; 73/863.31; 436/165, 174, 177, 180

(56) References Cited

U.S. PATENT DOCUMENTS

| 3,554,705 | A | | 1/1971 | Johnston et al. |
| 3,582,283 | A | | 6/1971 | Mirasol, Jr. |
| 4,162,896 | A | * | 7/1979 | Hosli |
| 4,239,746 | A | | 12/1980 | Bartos et al. |
| 5,273,907 | A | * | 12/1993 | Malmquist |
| 5,556,773 | A | * | 9/1996 | Yourno |
| 5,599,660 | A | * | 2/1997 | Ramanujam et al. |
| 5,620,662 | A | * | 4/1997 | Perlman |
| 6,083,761 | A | * | 7/2000 | Kedar et al. |

FOREIGN PATENT DOCUMENTS

| DE | 4419759 A1 | 12/1995 |
| EP | 0678745 A1 | 10/1995 |
| WO | WO9309872 | 5/1993 |
| WO | WO 95/26798 | 10/1995 |

* cited by examiner

Primary Examiner—William H. Beisner
(74) Attorney, Agent, or Firm—Birch, Stewart, Kolasch & Birch, LLP

(57) ABSTRACT

By arranging reagents needed for a specific reaction in separate distinct chambers in a reagent cartridge and combining several such reagent cartridges in a cassette in a format that matches that of commonly used microtitre plates. e.g. the 96 well format or other standard formats. several drawbacks of well-known procedures can be eliminated.

23 Claims, 4 Drawing Sheets

CARTRIDGE AND SYSTEM FOR STORING AND DISPENSING OF REAGENTS

This application is the national phase under 35 U.S.C. §371 of PCT International Application No. PCT/SE97/01562 which has an International filing date of Sep. 16, 19997 which designated the United States of America.

THE FIELD OF THE INVENTION

The present invention concerns a device and a procedure for storing and dispensing chemical reagents. In particular, the invention concerns a device and a procedure for storing and dispensing biochemical reagents used in small volumes and therefore sensitive to contamination, oxidation and cross-reactions between the reagents.

BACKGROUND OF THE INVENTION

Immunological methods such as RIA, EIA and ELISA have found widespread application in medical diagnostics during recent decades. (RIA, EIA and ELISA are abbreviations for Radioactive Immuno Assay, Enzyme Linked Immuno Assay and Enzyme Linked ImmunoSorbent Assay respectively). These methods quickly developed into standard procedures. To meet the demand for efficient handling with both manual and automated pipettes, as well as in detection instruments, standardised reaction vessels that could handle several samples at the same time were developed. These vessels are referred to as multi-sample plates in the remainder of this document.

A microtitre plate commonly consists of a rectangular plate formed from injection molded polystyrene plastic. The plate contains a number of hollows arranged in a grid. These hollows are known as wells and act as reaction vessels for individual chemical reactions. The three most important standards of microtitre plates are their outer dimensions that allow them to fit in standard instruments, their so-called grid spacing, which is the distance between the centre of one well to the centre of the adjacent well in the same row or column in the grid, and the position of the wells in relation to each other and to the outer edges of the plate. The most widely used microtitre plate format is approximately 128×85×14 millimeters with 96 wells arranged in a grid of eight rows and 12 columns. The grid spacing between wells is about nine millimeters. However, several other divisions are found within the above cited format. Usually encountered are also plates with 192, 384 or even more wells. Microtitre plates constituting one half of the above cited format are also in use. The most recent addition to this variety of multi-sample plates are the multi-sample plates used in so called multiple array technology, where extremely small volumes are ejected onto a surface, e.g. an absorbent surface. Examples of this technology include the multi-sample plates or sheets used in assays and procedures utilizing hybridization to High Density Oligonucleotide Arrays, e.g. detection of genetic mutations, genome screening or sequencing operations. Multi-sample plates used in the multi array technology are also referred to as nanotitre plates or nano-well plates. Also silicon chips or wafers, having areas for receiving reagents and samples, should be included under the definition "multi-sample plates".

Microtitre plates with wells arranged in a grid form are the most commonly used form of multi-sample plate. However, other arrangements of wells, such as circular forms, are also found in multi-sample plates.

When working routinely with microtitre plates, especially in areas of clinical application, the user aims to increase handling speed, i.e. the through-put speed of samples, by introducing various levels of automated system for the different steps. One such step is the handling of reagents.

Reagents can be handled with manually operated pipettes such as those known as plunger pipettes. For work with microtitre plates, multi-channel pipettes have been developed. These allow manual pipetting in complete rows or columns of wells in a single action. In aiming to further automate this pipetting work, a range of electronic instruments of varying complexity have also been developed. Examples include plunger pipettes with electronically driven step motors and multi-channel pipettes and dispensers with different types of pumps.

A high level of automation can be achieved by integrating units that position the reaction vessel in relation to the dispensing mouthpiece and units for the computerised control of this positioning in relation to the pipetting process. An instrument with such a high level of automation is usually called a pipetting robot. In other words, a pipetting robot comprises three main functional units. Firstly, a dispensing unit that comprises one or more individual precision pumps. The function of this type of precision pump is to dispense a specified volume of liquid through the mouthpiece at a specific time. Secondly, a pipetting robot comprises a positioning unit that orientates the position of the dispensing mouthpiece in relation to the reaction vessel at the exact moment of dispensing. Thirdly, an electronic control unit.

The difficulty in constructing a pipetting robot of the kind described in the previous paragraph is to achieve a sufficiently high level of precision regarding a number of key functions. One key function of a pipetting robot is the accuracy of the average amount of liquid dispensed and the standard deviation between different pipetting actions In general, the degree of accuracy is less when pipetting small volumes than when pipetting large volumes. A further key function is naturally the speed of operation measured as the number of completely dispensed samples per unit of time. It has proven difficult to construct robots that are both accurate when dispensing small volumes and sufficiently quick to meet the demands of molecular biological work in a clinical environment, for example.

In addition to these main functional characteristics of a pipetting robot, there are other characteristics that can also be important. Examples of such characteristics are purchase price, cost effectiveness for small series of samples, instrument size, and the requirement for cleaning the mouthpiece and other parts to help prevent contamination by foreign material and material from previous pipetting actions. In addition, the reaction vessel, the sample and the chemicals should be protected from exposure to air-borne particles that can carry such contaminating material.

Today, there are pipetting robots that differ with regard to whether they have separate mouthpieces for suction and dispensing or whether the same mouthpiece is used for both functions. The first type incorporates one or more suction mouthpieces connected with one or more liquid reservoirs, i.e. vessels from which the reagents shall be dispensed. These reagents pass from this vessel through the suction mouthpiece and via the dispenser unit to one or more dispensing mouthpieces from where they are transferred to the reaction vessel. This type of pipetting robot is subsequently referred to as a pump dispenser.

The second type of pipetting robot features one or more combined suction and dispensing mouthpieces. This type has a stand-alone liquid reservoir. The chemical reagents are drawn up from the sample vessel to the mouthpiece and are then dispensed into the reaction vessel with the same mouthpiece. This type of pipetting robot is subsequently referred to as a pipette dispenser.

The pump dispenser type of pipetting robot meets normal demands for accuracy, even when dispensing small volumes. It does not, however, fulfil the demands for speed of operation. In contrast, the pipette dispenser type of pipetting robot does meet normal demands for speed of operation. However, it does not normally meet the demands for a high degree of accuracy, which is one of the main pre-requisites.

A further problem is that neither type of pipetting robot is cost effective for small series of samples, i.e. handling about 500 samples or less. Protection against air-borne contamination can also be a problem. In addition, pump dispensers are very expensive to purchase and it is often difficult to clean their mouthpieces.

Those operations relevant to this invention that are today performed with conventional techniques, either manual or automatic, are, in chronological order the industrial synthesis of reagents, their storage in large packs, transport of these packs to the user, measuring out the relevant reagent volumes and dispensing these volumes in the appropriate sample wells or reagent vessels, such as the multi-sample plate, for example. When the actual sample has been applied and mixed with the reagents in the wells or equivalent intended for use in the multi-sample plate, this vessel is fully prepared and placed in an instrument or other location for incubation.

Pipetting robots are mainly used for two operations in this chain of events. They are used partly in connection with the industrial synthesis of reagents and their storage in large packs. These robots are frequently the pump dispensing type and are often large, expensive and relatively slow. They are, however, very accurate and form part of a quality-assured process with regard to all possible contamination threats, risks of mix-up, and similar hazards. Pipetting robots are also employed in the user's laboratory for measuring out relevant reagent volumes and dispensing these in, for example, a multi-sample plate where a certain analysis is to be performed. These pipetting robots can be of different types but they must be quick and cannot be bulky or expensive. For these reasons they are usually not as accurate as the former type mentioned. One problem in the user's laboratory can be the risk of contamination due to particles normally carried in the air, aerosols, splashing or via the mouthpiece or other component. The risk of mixing up bulk packs, for example, is especially great when many short series of samples are run or many different users are involved. In this context, sample means a patient sample, test material or other ingredient chosen by the user, of which the sample forms a part of the reagent mixture that is to be prepared.

It would be extremely advantageous if one could combine the advantages of the pipetting robot used in industrial context, i.e. accuracy and security with regards to contamination, mix-up and similar risks, with the advantages of the pipetting robot employed in the user's laboratory, i.e. speed, low price and compactness.

This could be achieved by replacing the storage of industrially synthesised reagents in bulk packs with storing the reagents directly in the end user's reaction vessel, which is then transported to the user's laboratory with the ready mixed reagents. Only ample application then takes place in the laboratory. This ensures rapid, accurate and secure handling in this environment. The need for a pipetting robot is thus eliminated and the advantages of low price and compact size can thus be considered to have been fulfilled.

This solution is nevertheless associated with two disadvantages. Firstly, different end users prefer different types and manufacturers of reaction vessels, which makes efficient industrial handing difficult. Secondly, pre-mixing the reagents in the reaction vessel can start various chemical processes that reduce sensitivity and shelf life, which can in turn lead to incorrect sample results.

The Prior Art

U.S. Pat. No. 3 554 705 describes a chemical package or crude reagent cartridge containing different reagents in separate storage chambers adapted for communication with, said compartments being closed with restraining means preventing the premature movement of the prepacked reagents from each of said storage chambers. This construction resembles the blister packaging system, used for solid and particulate matter. Although no volumes are mentioned in the description and claims, the construction of the storage chambers makes it clear, that they are intended to contain volumes in the order of magnitude of milliliters and in no case volumes so small, that they resist gravity and require centrifugation to leave the cartridge.

EP 678 745 A1 represents a more recent approach where a sample is transferred through centrifugation from a pointed vessel to a reaction vessel, where the latter is covered by a membrane and the pointed vessel penetrates said membrane. This system does not, however, concern the storage and dispensing of reagents and lacks the benefits, associated with the present invention.

A number of special problems arise when using the extremely small volumes that are typical in this context, i.e. in the order of a few $\mu l$ and less. For example, the volumes are so small that a force is required to detach them from the sides of the vessel or container in which they are stored. These volumes are often protected from evaporation and oxidation by a layer of wax or viscous oil. In practice, a force greater than gravity is needed to transfer the reagent from the dispensing container or device to the reaction vessel.

The aim of the present invention is to provide a device that conforms with current standards and working methods, especially those applied in biochemical analysis. Biochemical analysis refers to procedures to detect biochemical components, e.g. proteins, enzymes, and oligonucleotides, or for detecting the presence of specific cells, e.g. disease-causing organisms or cells that have undergone a pathogenic transformation, such as cancer cells. In particular, the aim of the invention is to provide a system that permits the safe and contamination-free storage of reagents, accurate dispensing with a high level of reproducibility, and simple handling that minimises the number of user operational steps. One aim is to eliminate the need for manual or automated pipetting by the user, i.e. in the laboratory where the analysis is performed.

SUMMARY OF THE INVENTION

The drawbacks of current techniques described above are overcome by the present invention as described in the attached claims. In particular, the invention concerns a device and a procedure for storing and dispensing biochemical reagents used in small volumes and therefore sensitive to contamination, oxidation and cross-reactions between the reagents.

BRIEF DESCRIPTION OF THE DRAWINGS

The invention is described in greater detail with reference to the enclosed drawings, in which.

DESCRIPTION OF THE INVENTION

According to the invention, the reagents are stored and dispensed using a device capable of containing two or more reagents, separated from each other and protected from the atmosphere. The reagents are then removed from the device through centrifigation, optionally after mechanically removing or relocating means, such as covers, closures or barriers sealing the chambers of the device. Said means can include plugs or valves, films, membranes and also viscous liquids or waxes.

The reagent chambers according to the present invention comprise any distinct, physically separated volume, generally containing volumes less than about 100 µl. In wash steps, the volume can nevertheless be larger, e.g. 200–500 µl. In specific, preferred embodiments, the volumes are considerably smaller, in the interval of 0.001–0.5 µl.

Figure 1A:
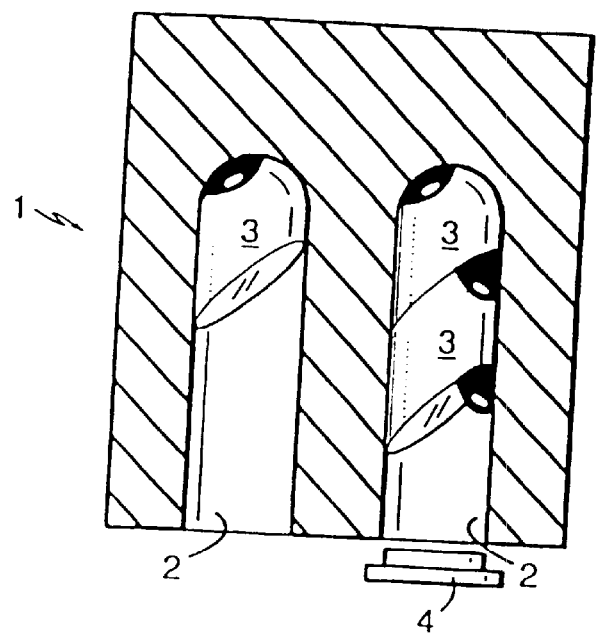
FIG. 1*a* shows a schematic cross-section of a reagent cartridge according to the present invention.

FIG. 1*a* shows schematically a reagent cartridge (1) with its distinct chambers (2), in which small amounts of reagents are stored. These reagents are marked in black. The reagents are separated from each other and from the surrounding atmosphere by seals (3) of appropriate material such as wax or viscous organic compounds. The chambers (2) can themselves be sealed off with other types of closures (4) such as plugs or thermoplastic membranes.

Figure 1B:
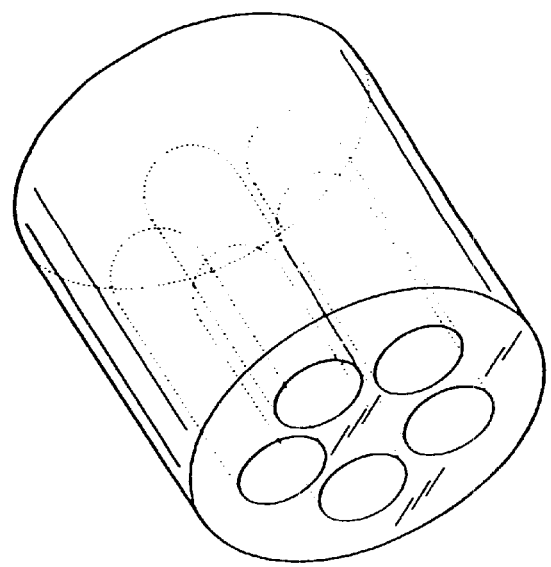
FIG. 1*b* shows a perspective view of the cartridge in FIG. 1*a*.

FIG. 1*b* shows the above embodiment in a perspective view, illustration one spatial arrangement of the chambers. Obviously the number and configuration of the chambers can vary within the scope of the invention.

Figure 2:
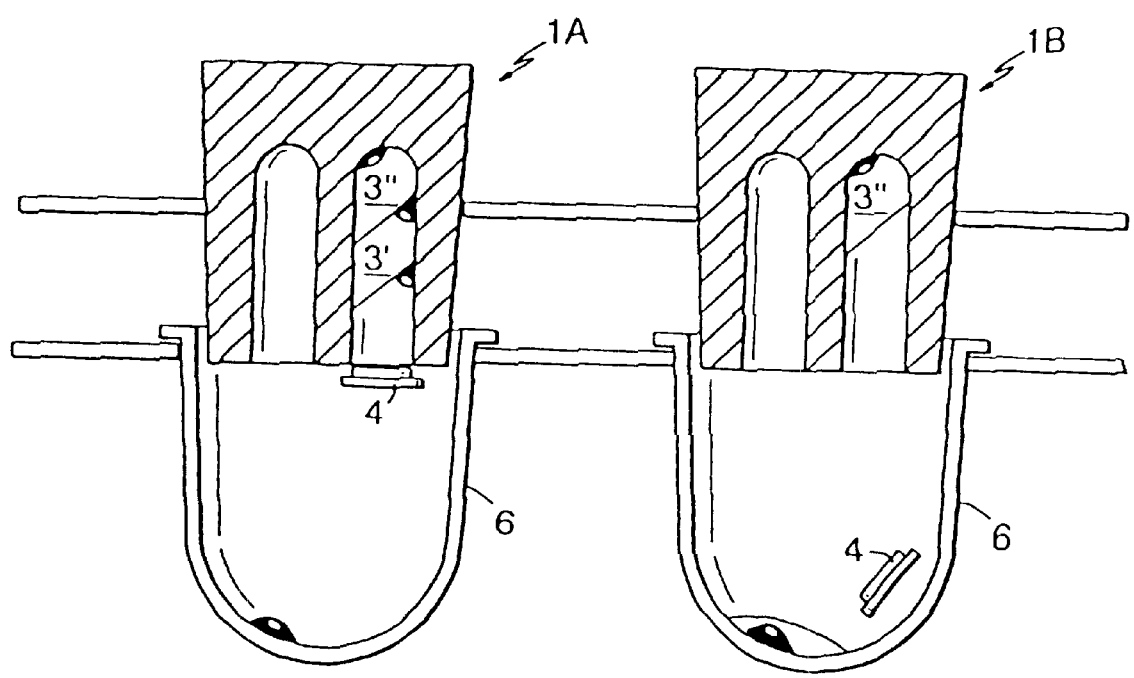
FIG. 2 shows schematically how reagent cartridges can be combined with a multi-sample reaction plate according to the invention.

FIG. 2 shows how more than one reagent cartridge (1A and 1B) can be arranged on the holder of a cassette so that the numbers and positions of the reagents cartridges match the numbers and positions of the reaction vessels in the multi-sample plate into which the reagents are to be dispensed, 1A and 1B show two distinct stages of operation. In reagent cartridge 1A, the seal of the left-hand chamber has been detached and the reagent transferred to the vessel, while the seal 4 of the right-hand chamber is still in place and all the reagents and their sealing layers (3', 3") remain in place. In 1B, seals 4 and 3' have been removed, but seal 3" and the final reagent remain.

Figure 3A:
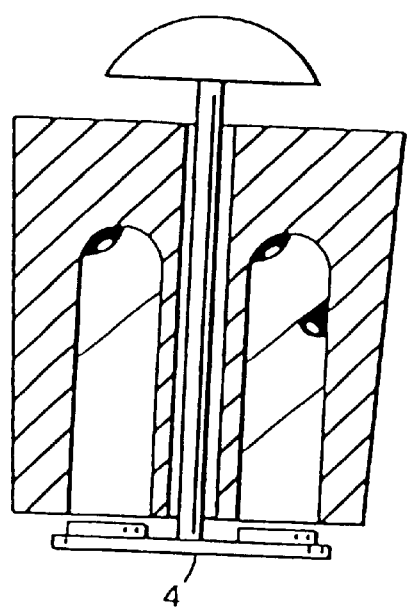
FIGS. 3A and 3B show two embodiments of the invention.
Figure 3B:
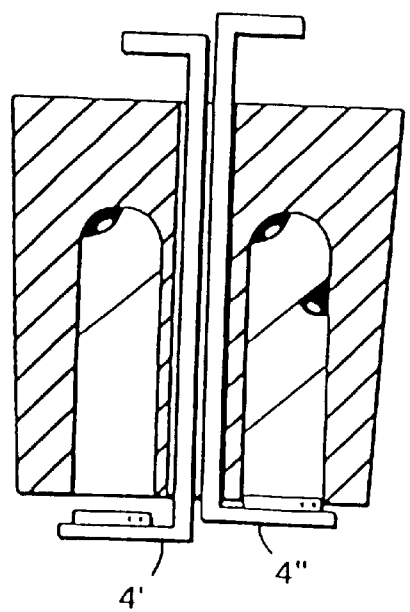

According to an embodiment of the invention, the reagent chambers can additionally be closed by a detachable or movable cover, plug or a breakable seal or film. FIGS. 3A and 3B show schematically two embodiments of the invention where seal 4 is operated and opened mechanically. 3A shows one embodiment where all seals open simultaneously. 3B shows another embodiment that allows seals to be opened independently of each other.

One embodiment, concerning the opening of the closing means, comprises plates with a three-dimensional pattern, e.g. grooves and ridges, engaging with parts of the closing means, extended through the reagent cartridge (FIG. 3A and B). These plates will be called "press-plates" in the following. Such a press-plate can be designed in various fashion, for example be assigned color codes, corresponding to different weights and/or patterns. Preferably, these press-plates are actuated during the centrifugation of the assembly consisting of a receiving multi-sample plate, reagent cartridges and press-plate. Optionally, the press-plate can be depressed manually with or without mechanical aids. The benefit of actuation by centrifugation or using optional mechanical aids, is that the opening of the cartridges, corresponding to the pattern of the press-plate, is guaranteed to be simultaneous and to include all cartridges concerned.

Figure 4:
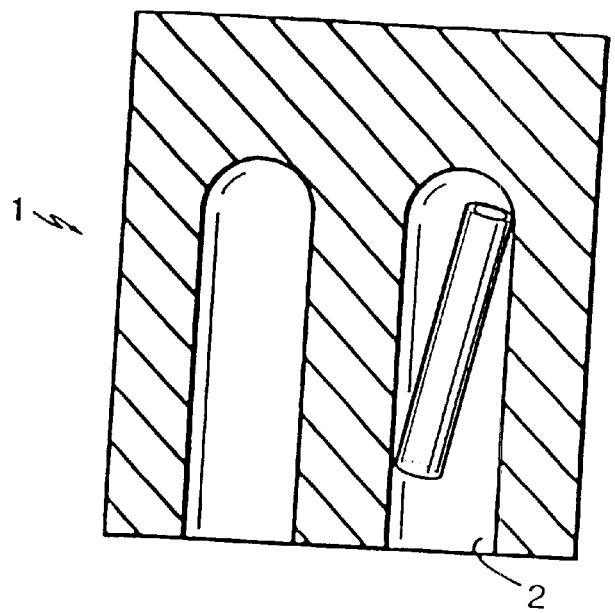
FIG. 4 shows a schematic cross-section of an embodiment where one of the reagents is enclosed in an open-ended capillary, contained in one of the chambers.

According to one specific embodiment, shown schematically in FIG. 4, one or several of the reagents is enclosed in an open-ended capillary, contained in one of the chambers. This is specially preferred when dispensing very small volumes of reagent, e.g. volumes in the interval of 0.001–0.50 µl. This arrangement is also beneficiary in protecting a small reagent volume from environmental influences. Volumes in this interval are further very difficult to measure exactly, as physical interactions, such as surface tension, adsorption and hydrodynamic behaviour exert a considerable influence on the droplet.

In measuring, storing and dispensing extremely small volumes, for example volumes less than 50 nanoliters, special difficulties are encountered. As previously described, such volumes are hitherto handled in a satisfactory manner only by ink-jet like apparatuses. It has been shown, by the present inventor, that the behaviour of such small volumes is dependent on the relation between volume and the surface area in contact with said volume. For example in the filling and cutting of thin capillaries, the cutting itself causes a compression of the capillary and thus a displacement of liquid. Surprisingly, when the surface area in contact with the liquid is maximized, for example by using a longer and thinner capillary in stead of a shorter and thicker, the deformation during cutting and thus liquid displacement is reduced. It is particularly preferred to introduce a core in the capillary and thus form a volume, enclosed by the outer walls of the core and the inner walls of the capillary. This is true regardless of shape of the capillary, however, circular or oval cross sections have practical benefits. Additionally, when extending the length of the liquidfilled sections, the effect of the cutting has less effect on the accuracy. The technology of cutting segments of a predetermined length is also well developed and high accuracy and reproducibility is acheived.

The capillary in FIG. 4 can also, within the scope of the present invention, be a multi-lumen capillary, suitable for independent introduction in a reaction vessel or constitute part of a reagent cartridge, as a capillary contained in one chamber of a cartridge.

Figure 5:
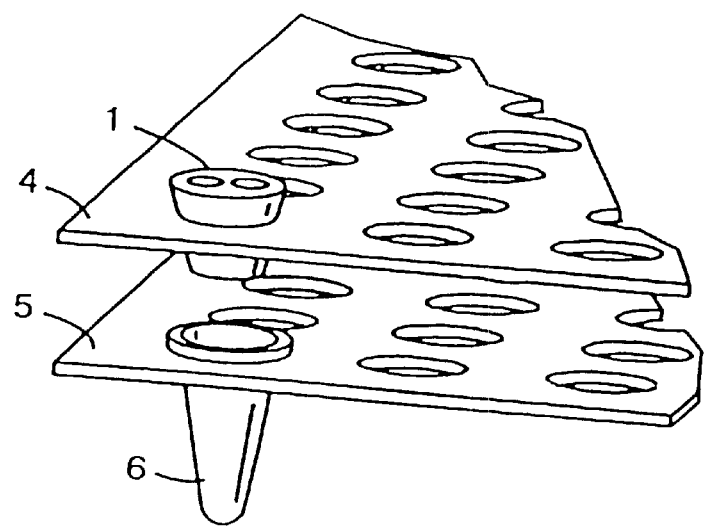
FIG. 5 shows a cut-away perspective view of one preferred embodiment of the invention where the reaction cartridges are arranged in the same numbers and positions as the reaction vessels in a multi-sample plate known as a microtitre plate.

FIG. 5 indicates one preferred embodiment of the invention, i.e. a cassette where several reagent cartridges are arranged so that their numbers and positions match the numbers and positions, or fractions of said numbers and positions of the reaction vessels in a multi-sample plate such as a microtitre plate. Ideally, the reagent cartridges are arranged in rows of eight and columns of twelve in one cassette that can be placed on or partially in a microtitre plate of the commonly used 96 well format. It is however contemplated, that the cartridges correspond to a fraction of this or other commonly used formats. Reagent cartridges can be assembled in cassettes comprising 3×8 cartridges or in strips of cartridges, single file, of various lengths.

When producing the reagent cartridges according to the invention, they may comprise separate units when being filled with reagents, yet are suitable for combining in a cassette so that several can be used together. This allows effective and flexible production, especially in cases, where the cartridges are filled with different reagents or different reagent concentrations. Thus, a large series of cartridges with identical or similar composition can be produced to be later combined in cassettes intended for specific analyses. A simple example of this is the production of a cassette to use in an optimisation reaction. Large series of reagent cartridges with different concentrations of a reagent can be produced and then arranged as concentration gradients in the different rows or columns of the multi-sample plate.

The seals to the open chambers referred to previously are suitable for opening by any of the following means: increased temperature, centrifuging the reagent cartridge or application of an external force. Increasing temperature, for example, can involve allowing the temperature of the reagent cartridge to rise from a storage temperature of 18 18° C. or below to a temperature of −4° C. +8° C., or +20° C., or heating it to a higher temperature. Centrifugation can be performed at different speeds so that the force used to open the seals can be controlled. Arrangements for applying external force cover any kind of mechanical influence, including the previously described "press-plates".

According to one preferred embodiment, the reagent cartridge includes at least one of the following reagents: DNA polymerase, RNA polymerase, reverse transcriptase, urasil-N-glycolase, DNA ligase, catalytic ribonucleic acid, deoxyribonucleotides, ribonucleotides, oligonucleotides, fluorescent dyes, bovine serum albumin, formamide, glycerol, buffer substances, ammonium sulphate, dimethylsulphoxide, anionic detergents, and non-ionic detergents for a specific reaction.

The invention also comprises a system for storing and dispensing chemical reagents, especially small volumes of biochemical reagents. It is characterised by the reagents being located in distinct chambers in a reagent cartridge and isolated from the surrounding atmosphere, and by the arrangement of several similar reagent cartridges so that their numbers and positions reflect the numbers and positions of reaction vessels known as wells contained in a multi-sample plate.

Reactions whose execution is especially suitable for using this reagent cartridge or system according to the described invention are as follows: A polymerase chain reaction (PCR), a ligase chain reaction (LCR), a "gapped-LCR-reaction", a nucleic acid sequence-based amplification (NASBA), a self-sustained sequence replication (3SR), a transcription mediated amplification (TMA), a strand displacement amplification (SDA), a target amplification, a signal amplification, or a combination of any of the above.

A reagent cartridge or system according to the present invention is especially applicable for detecting a nucleotide sequence or nucleotide sequences forming part of any of the following nucleic acids: a virus genome, nucleic acids originating in bacterial cells or eukaryotic cells, or coding regions from cells of vertebrates used for tissue typing.

A reagent cartridge or system according to the presented invention is especially applicable for detecting any of the following viruses: human immunodeficiency virus (HIV), human papillomavirus, hepatitis viruses, cytomegalovirus or similar.

A reagent cartridge or system according to the presented invention is especially applicable for detecting cells from any of the following genera: Chlamydia, Rickettsia, Mycobacterium, Haemophilus, Neisseria. Streptococcus, Listeria, Cryptococcus. Coccoides, Blastomyces, Histoplasma or similar.

A reagent cartridge or system according to the presented invention is especially applicable for detecting cancer cells.

The present invention further comprises kits for performing any one of the reactions or assays described above, such a kit comprising the necessary reagents, prepacked in cartridges optionally assembled as one or several cassettes, optionally reaction vessels and actuating means such as press-plates and instructions for use.

One preferred embodiment of the invention is a cassette used when performing chemical reactions, particularly biochemical analyses using multi-sample plates known as microtitre plates. It is characterised by the cassette consisting of a number of reagent cartridges arranged so that their numbers and positions match the numbers and positions of reaction vessels known as wells contained in a multi-sample plate such as the conventional 96 hole microtitre plate format.

Finally, the invention includes a procedure for dispensing reagents, principally biochemical reagents used in small amounts during analyses that employ multi-sample plates. This procedure includes the following steps:

at least two reagents are delivered, physically separated from each other in a reagent cartridge, several reagent cartridges are arranged in at least one cassette so that their numbers and positions match the numbers and positions, or fractions of said numbers and positions, of reaction vessels in a multi-sample plate such as a microtitre plate, the cassette or casettes is/are combined with a multi-sample plate, the reagent cartridges are emptied of their contents.

According to one preferred embodiment, emptying takes place in several steps, for example, by the sequential execution of one or more of the following measures: increasing temperature, centrifugation, and application of an external force.

Although the invention has been described with regard to its preferred embodiments, which constitute the best mode presently known to the inventors, it should be understood that various changes and modifications as would be obvious to one having the ordinary skill in this art may be made without departing from the scope of the invention which is set forth in the claims appended hereto.

What is claimed is:

1. A reagent cartridge for storing and dispensing biochemical reagents used in such volumes that centrifugation is required to detach the reagents from the cartridge, comprising at least two separate distinct chambers for reagents suitable for direct addition to a reaction system; and a seal in at least one o f the chambers that seals the reagent from the surrounding atmosphere, whereby the reagent cartridge can be combined in a cassette comprising of several reagent cartridges.

2. The reagent cartridge according to claim 1, wherein at least one of the chambers has an orifice that can be sealed with a openable closure that can be opened without affecting the surroundings of the orifice or other sealed chambers arranged in the same device.

3. The reagent cartridge according to claim 2, wherein the sealed closure is opened by increasing temperature, centrifugation, application of an external force or a combination thereof.

4. The reagent cartridge according to claim 1, wherein the reagent volumes are in the range of 1 to 200 µl.

5. The reagent cartridge according to claim 1, further comprising at least one of th e following reagents: DNA polymerase, RNA polymerase, reverse transcriptase, urasil-N-glycolase, DNA ligase, catalytic ribonucleic acid, deoxyribonucleotides, ribonucleotides, oligonucleotides, fluorescent dyes, bovine se rum albumin, formamide, glycerol, buffer substances, ammonium sulphide, dimethylsulphoxide, anionic deter gents, or non-ionic detergents.

6. The reagent cartridge according to claim 1, wherein a separate capillary is contained in at least one of said fluid chambers.

7. The reagent cartridge according to claim 6, wherein the separate capillary is a multi-lumen capillary.

8. The reagent cartridge according to claim 6, wherein the separate capillary comprises an outer wall and a core, defining the capillary space between the wall and core.

9. A system for storing and dispensing biochemical reagents in cartridges, said reagent volumes requiring centrifugation to be detached from said cartridges, comprising reagents located in distinct chambers in a reagent cartridge and isolated from the surrounding atmosphere, wherein several such reagent cartridges are arranged so that their numbers and positions reflect the numbers and positions or fractions of reaction vessels known as wells contained in a multi-sample holder.

10. The system according to claim 9, wherein the reagent cartridges are arranged in rows and columns according to conventional microtitre plate format or other standard formats.

11. The system according to claim 9, wherein at least one of the reagents is supplied in the form of a concentration gradient by arranging the reagents in different concentrations in different reagent cartridges.

12. The system according to claim 9, wherein said reagents are reagents for at least one of the following reactions: a polymerase chain reaction (PCR), a ligase chain reaction (LCR), a "gapped-LCR-reaction", a nucleic acid sequence-based amplification (NASBA), a self-sustained sequence replication (3SR), a transcription mediated amplification (TMA), a strand displacement (SDA), target amplification, a signal amplification, or a combination of any of the above.

13. The system according to claim 12, wherein said reagents are for the determination of the presence or absence of a nucleotide sequence or nucleotide sequences, and wherein the nucleotide sequence or nucleotide sequences are part of any of the following nucleic acids: a virus genome, nucleic acids originating in bacterial cells or eukaryotic cells, or coding regions from cells of vertebrates used for tissue typing.

14. The system according to claim 9, wherein said reagents are for the detection of any one of the following viruses: human immunodeficiency virus (HIV), human papillomavirus, hepatitis viruses, or cytomegalovirus.

15. The system according to claim 9, wherein said reagents are for the detection of cells of any of the following genera: Chlamydia, Rickettsia, Mycobacterium, Haemophilus, Neisseria, Streptococcus, Listeria, Cryptococcus, Coccoides, Blastomyces, or Histoplasma.

16. The system according to claim 9 wherein said reagents are or the detection of cancer cells.

17. A cassette comprising reagent cartridges used to perform biochemical reactions using reagents in volumes requiring centrifugation to detach the reagents from the cartridge, comprising a number of reagent cartridges according to claim 1 arranged so that their numbers and positions match the numbers and positions or fractions of said numbers and positions of reaction vessels known as wells in a multi-sample plate.

18. The cassette according to claim 17, wherein the reagent cartridges are arranged in rows and columns according to the conventional microtitre plate format or other standard formats.

19. A method for dispensing reagents which comprises delivering at least two reagents that are physically separated from each other into a reagent cartridge, so that at least one of the reagents in the reagent cartridge is contained in a chamber having a seal that seals the reagent from the surrounding atmosphere, wherein several reagent cartridges are arranged in a cassette so that their numbers and positions match the numbers and positions of fractions of the numbers and positions of reaction vessels in a multi-sample plate, combining at least one cassette containing the reagent cartridge with a multi-sample holder, emptying the reagent cartridge their contents by centrifugation.

20. The procedure for dispensing reagents according to claim 19, wherein the cartridges are emptied in several steps.

21. The procedure for dispensing reagents according to claim 20, wherein the cartridges are emptied by the sequential execution of one or more of the following measures: increasing temperature, centrifugation, application of an external force or a combination thereof.

22. A method of preparing a cassette system for dispensing reagents which comprises delivering at least two reagents that are physically separated from each other into a reagent cartridge, so that at least one of the reagents in the reagent cartridge is contained in a chamber having a seal that seals the reagent from the surrounding atmosphere, wherein several reagent cartridges are arranged in a cassette so that their numbers and positions match the numbers and positions of fractions of the numbers and positions of reaction vessels in a multi-sample plate.

23. A method of dispensing reagents which comprises combining at least one cassette of claim 17 with a multi-sample holder, emptying the reagent cartridge their contents by centrifugation.

* * * * *